United States Patent [19]
Cornellier

[11] Patent Number: 5,330,453
[45] Date of Patent: Jul. 19, 1994

[54] FEMININE URINARY AID

[76] Inventor: Maurice H. Cornellier, P.O. Box 2123, Inverness, Fla. 34451

[21] Appl. No.: 100,265

[22] Filed: Aug. 2, 1993

[51] Int. Cl.$^5$ ............................................. A61F 5/44
[52] U.S. Cl. ........................................ 604/329; 4/144.2; 222/527
[58] Field of Search .............. 604/329; 4/144.1, 144.2, 4/451; 222/526, 527; 141/297, 331, 337

[56] References Cited

U.S. PATENT DOCUMENTS

| D. 208,609 | 9/1967 | Garland . |
| 2,734,198 | 2/1956 | Kutsche . |
| 2,878,486 | 3/1959 | Bartlett et al. . |
| 3,535,714 | 10/1970 | Bjork ........................... 4/144.2 |
| 3,572,318 | 3/1971 | Garland . |
| 3,613,123 | 10/1971 | Langstrom . |
| 3,731,869 | 5/1973 | Griffin . |
| 3,964,111 | 6/1976 | Packer . |
| 4,023,216 | 5/1977 | Li . |
| 4,108,222 | 8/1978 | Kaufman . |
| 4,528,703 | 7/1985 | Kraus . |
| 4,681,573 | 7/1987 | McGovern et al. . |
| 4,734,941 | 4/1988 | DeWitt et al. . |
| 4,751,751 | 6/1988 | Reno . |
| 4,815,151 | 3/1989 | Ball . |
| 4,937,890 | 7/1990 | Tafur . |
| 5,091,998 | 3/1992 | Irazabal . |

*Primary Examiner*—Randy C. Shay
*Attorney, Agent, or Firm*—Barnes, Kisselle, Raisch, Choate, Whittemore & Hulbert

[57] ABSTRACT

A feminine urinary aid that includes a one-piece body of water resistant biodegradable cellulose composition having a pair of flat side portions with elongated parallel linear side edges. The side portions are integrally joined to each other along contiguous side edges, and a triangular end portion is integrally joined to the side portions at end edges of the side portions that are perpendicular to the side edges. The end portion of the body thus closes one end of the body and imparts a V-shaped cross section to the body as viewed in a direction parallel to the side edges. This V-shaped body may be positioned by a female in the genital region beneath the urethra while in the standing position for receiving urine, and either retaining the urine or directing the urine away from the body.

12 Claims, 2 Drawing Sheets

FEMININE URINARY AID

The present invention is directed to devices for assisting human females to urinate when sanitary facilities are unavailable, and more particularly to a device for assisting a human female to urinate in a standing position.

BACKGROUND AND SUMMARY OF THE INVENTION

There are many instances in which sanitary facilities for female urination are unavailable in the sense of being either unsanitary, overcrowded or completely lacking. For example, at public events such as concerts or sporting events, the facilities provided often have less than desired cleanliness or availability. When camping or hiking, for example, facilities are often completely lacking.

It is a principal object of the present invention to provide a device that will aid or assist a human female to urinate while standing. Another and more specific object of the present invention is to provide a device of the described character that is easy to use, that is disposable and biodegradable, that is economical to manufacture, and/or that is easily foldable for carrying or for sale in a vending machine. Another object of the present invention is to provide a self-contained feminine urinary aid, particularly adapted for use in an emergency situation in the absence of available toilet facilities, which will retain and hold a quantity of urine for later disposal.

A feminine urinary aid in accordance with the present invention includes a one-piece body of water resistant biodegradable water soluble composition having a pair of flat side portions with elongated parallel linear side edges. The side portions are integrally joined to each other along contiguous side edges, and a triangular end portion is integrally joined to the side portions at end edges of the side portions that are perpendicular to the side edges. The end portion of the body thus closes one end of the body and imparts an open V-shaped cross section to the body as viewed in a direction parallel to the side edges. This V-shaped body may be positioned by a female in the genital region beneath the urethra while in the standing position for receiving urine, and either retaining the urine or directing the urine away from the body.

In some preferred embodiments of the invention, creases are formed in the body to extend along the side edges where the side portions are joined, the end edges where the side portions are joined to the end portion, and centrally through the end portion to facilitate folding of the device into a flat geometry in which the side portions are parallel and adjacently facing each other. The device or aid may be readily packaged in this flat condition for sale in quantity in a box or individually at a dispensing machine, and for transport in a purse, backpack or the like. The foldable device may have an open second end so as to operate as a funnel for directing urine away from the body during use. In other embodiments of the invention, the second end of the body is closed to form a V-shaped cup-like construction, which may be either open for retention and immediate disposal of urine, or filled with water absorbent material to retain the urine for later disposal when convenient. In the latter case, a thin gauze-like sheet covers the water absorbent material and is affixed to the side portions for retaining the material in the body for later disposal.

BRIEF DESCRIPTION OF THE DRAWINGS

The invention, together with additional objects, features and advantages thereof, will be best understood from the following description, the appended claims and the accompanying drawings in which:

DETAILED DESCRIPTION OF PREFERRED EMBODIMENTS

Figure 1:
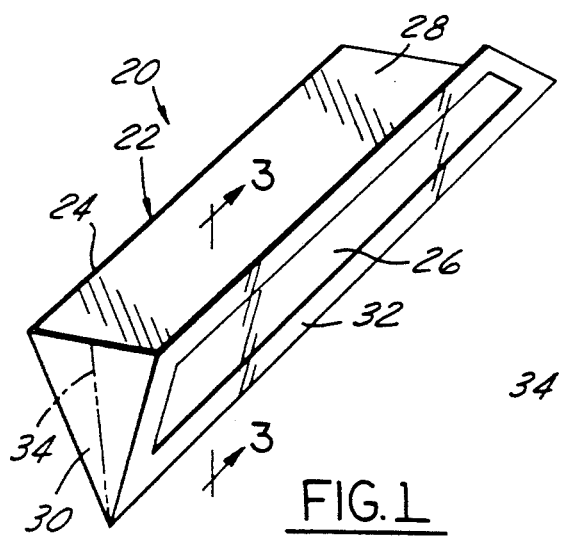
FIG. 1 is a perspective view of a feminine urinary aid in accordance with one presently preferred embodiment of the invention.
Figure 2:
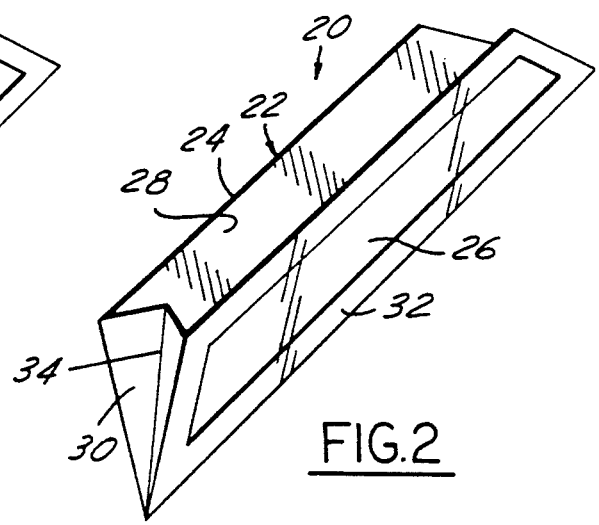
FIG. 2 is a perspective view of the device in FIG. 1 in a partially folded condition.
Figure 3:
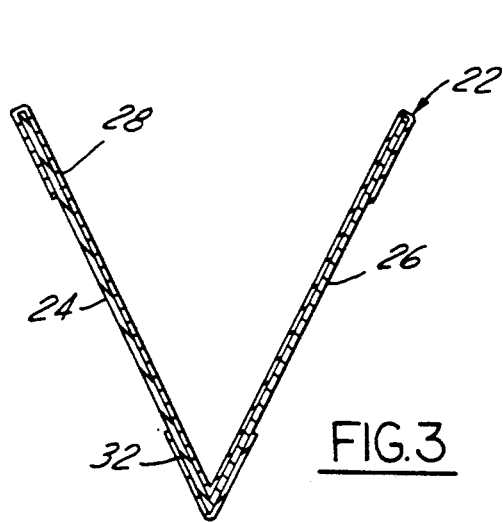
FIG. 3 is a sectional view taken substantially along the line 3—3 in FIG. 1.

FIGS. 1-3 illustrate a device 20 in accordance with one presently preferred embodiment of the invention as comprising a one-piece body 22 having integrally joined side sections or portions 24,26 and one end portion or section 28. Side portions 24,26 each comprise a section of relatively thick biodegradable cellulose (paper) composition having spaced parallel upper and lower side edges, with the lower side edges being integrally joined to each other. A relatively thin and flexible liner 28 is joined to sidewall sections 24,26, and is folded over the upper side edges and joined to the outer faces to reinforce the construction. In the same way, a reinforcing section 30 externally extends along the joined side edges of side sections 24,26. End section 28 is integrally joined to side sections 26 along the end edges of the side sections to close one end of body 22, and to impart to the body the open generally V-shaped cross section illustrated in FIG. 3. The opposing end of the body is open, with the parallel end edges of side sections 24,26 being angulated away from end portion 28 in the direction of the joined contiguous side edges. At least liner 28 and end portion 30, and preferably the entire body 22, are of biodegradable cellulose material that is either compounded or treated to be water repellant for at least a short time duration. Body 22 is creased along the contiguous and integrally joined lower side edges of side sections 24,26, along the contiguous and integrally joined end edges of side sections 24,26 where joined to end section 30, and centrally at 34 along end section 30. In this way, body 22 may be folded, as partially shown in FIG. 2 into a flat geometry in which end portion 30 is folded and contained between side portions 24,26, with the latter being in parallel abutting and facing engagement with each other.

In use, the folded device is removed from the package in which it is initially contained, and unfolded to the orientation and geometry illustrated in FIG. 1. The device thus forms a funnel-like construction that is closed at one end and open at the other. The closed end of the device is placed by hand beneath the urethra so that, in use, the stream of urine is directed in an uninterrupted flow along the length of the device and away from the user's body. Preferably, side sections 24,26 are thicker than end section 30 and relatively stiff except where creased to facilitate use. It will be appreciated, of course, that stiffness of side sections 24,26 as compared with end section 30 is a relative term, meaning that the side sections do not fold or buckle when subjected to ordinary use.

Figure 4:
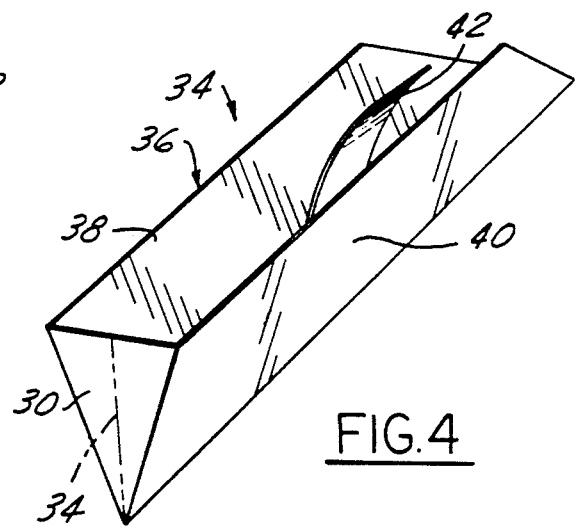
FIG. 4 is a perspective view of a modification to the embodiment of FIG. 1.

FIG. 4 illustrates a modified device 34 in which the integral one-piece body 36 has side sections 38,40 of relatively thinner construction than the embodiment of FIG. 1-3, but still joined to each other along lower edges of the side sections and joined to end section 30 along the end edges of the side sections. A tab or flap 42 extends from the upper side edge of side section 40 to function as a handle during use. As with the other embodiments of the invention, body 36 is of water-repellant biodegradable cellulose construction.

Figure 5:
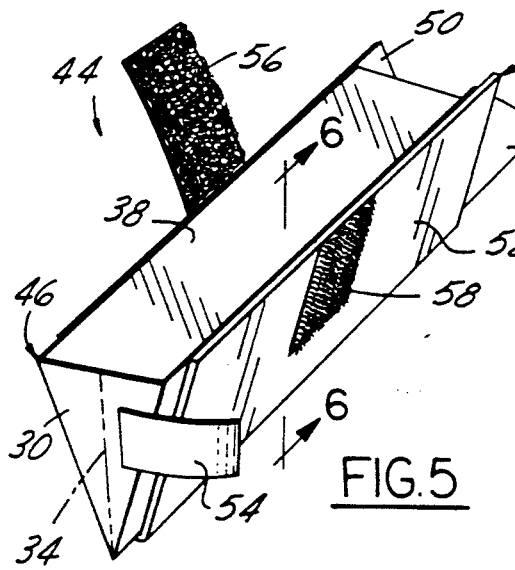
FIG. 5 is a perspective view of another modified embodiment of the invention.
Figure 6:
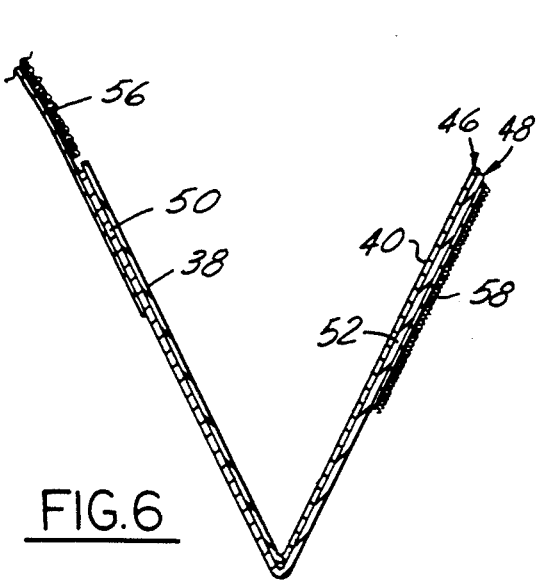
FIG. 6 is a sectional view taken substantially along the lines 6—6 in FIG. 5.
Figure 7:
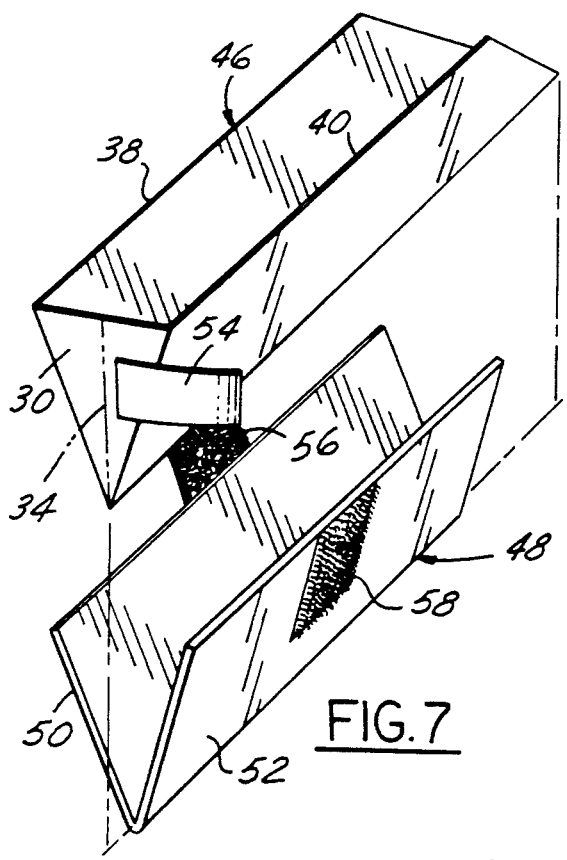
FIG. 7 is an exploded perspective view of the device illustrated in FIGS. 5-6.

FIGS. 5-7 illustrate a urinary aid 44 in which the body 46 is similar to that in FIG. 4 but with handle 42 deleted. A non-disposable holder 48 comprises a pair of holder side 50,52 sections of cellulose or plastic integrally joined to each other along a contiguous side edge of each holder section with the end edges being open. Body 46 may be received and nested within holder 48 between side sections 50,52. Holder 48 is of relatively thicker and stiffer construction than body 46 of device 44, and provides support during use. A tab 54 extends from end wall 30 of body 46 to engage an end edge of side section 52 and prevent body 46 from sliding out of holder 48 during use. A tab 56 that extends from holder side section 50 cooperates with an external pad 58 on holder side section 52 to form a hook-and-loop fastener for holding the holder side sections in a closed position, either with or without a body 46 being captured therebetween for transport when not in use.

Figure 8:
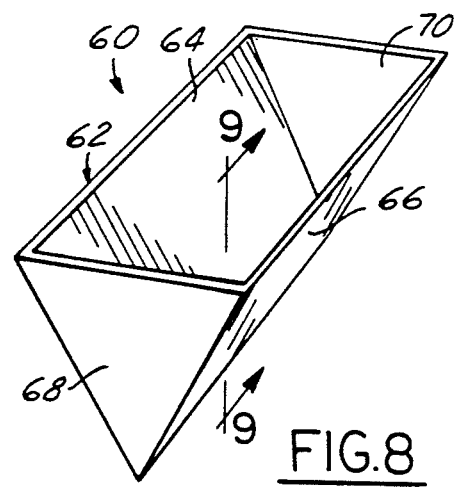
FIG. 8 is a perspective view of a further embodiment of the invention.
Figure 9:
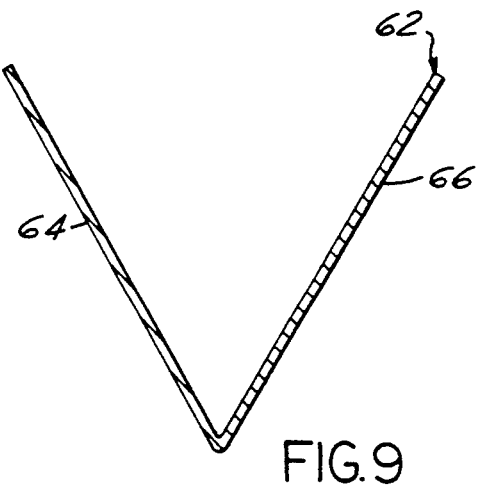
FIG. 9 is a sectional view taken substantially along the line 9—9 in FIG. 8.

FIGS. 8 and 9 illustrate an embodiment 60 of the invention in which the body 62 has side sections 64,66 and integral end sections 68,70 that close the two ends of the body while maintaining the open V-shaped cross section that characterizes the present invention. End sections 68,70 are parallel to each other and perpendicular to the side edges of side sections 64,66. The body 62 is of relatively stiff non-foldable construction, while still being of water-repellant biodegradable cellulose composition. The open cup-like V-shaped cross section of the body 62 may be held beneath the urethra to receive and retain urine, which may be discarded when full. Body 62 may be either discarded, or rinsed and retained for reuse if desired.

Figure 10:
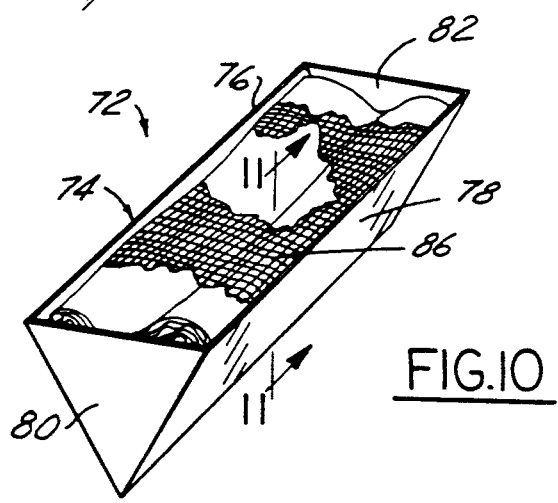
FIG. 10 is a fragmentary perspective view of yet another embodiment of the invention.
Figure 11:
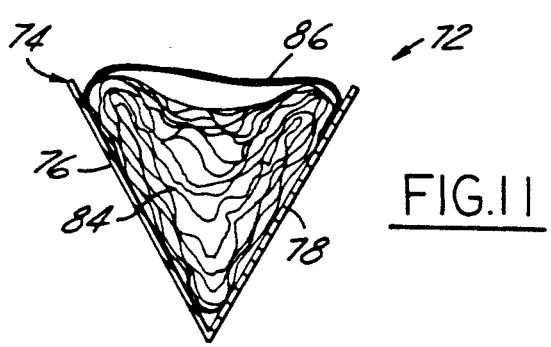
FIG. 11 is a sectional view taken substantially along the line 11—11 in FIG. 10.

FIGS. 10-11 illustrate an embodiment 72 of the present invention that again includes an open v-shaped body 74 with side sections 76,78 and end sections 80,82 similar to body 62 in FIGS. 8-9. In this embodiment, the open V-shaped cross section of the body filled with water-absorbent cellulose material 84 of construction similar to a conventional disposable diaper. The open upper mouth of body 74 is covered by a thin water-pervious gauze-like material 86 that retains material 84 within body 74 before, during and after use. Material layer 86 is fastened to the inside of the upper side edges of side sections 76,78, as illustrated in FIG. 11. The embodiment of FIGS. 10-11 is particularly adapted to retain and hold for later disposal a quantity of urine in emergency situations in which no toilet facilities are available.

I claim:

1. A feminine urinary aid that comprises a one-piece body of water resistant biodegradable water soluble composition, said body having a pair of flat side portions each with elongated parallel linear side edges and one end edge perpendicular to said side edges, said side portions being integrally joined to each other along contiguous side edges of said portions, the other side edges of said side portions being free side edges, and a triangular end portion integrally joined to said side portions at said end edges so as to close one end of said body and impart an open-topped V-shaped cross section to said body viewed in a direction parallel to said side edges.

2. The aid set forth in claim 1 further comprising creases extending along said end edges of said flat side portions where joined to said end portion, along said side edges where joined to each other, and centrally through said end portion perpendicular to said joined side edges to facilitate folding of said aid into a flat geometry in which said side portions are parallel and adjacent to each other.

3. The aid set forth in claim 2 wherein said body has an open second end spaced from said one end.

4. The aid set forth in claim 3 wherein said side portions are of stiffer less flexible construction than said end portion.

5. The aid set forth in claim 3 further comprising a handle integrally extending from one of said side portions to facilitate holding of the aid during use.

6. The aid set forth in claim 3 further comprising a holder of stiffer less flexible composition than said body, said holder being of V-shaped cross section with open ends and being contoured to receive and hold said body during use.

7. The aid set forth in claim 6 wherein said body includes means for engaging said holder and locating said body in said holder during use of said aid.

8. The aid set forth in claim 7 wherein said holder includes means for fastening said holder in a flat folded geometry during non-use.

9. The aid set forth in claim 3 wherein said side portions of said body each have a second end edge remote from said one end edge, said second end edges being angulated away from said end portion toward said contiguous side edges.

10. The aid set forth in claim 1 wherein said side portions each have a second end edge spaced from said one end edge, and wherein said body further comprises a second triangular end portion integrally joined to said side portions at said second end edges so as to close the other end of said body spaced from said one end.

11. The aid set forth in claim 10 further comprising means of water-absorbent construction contained within said V-shaped cross section of said body.

12. The aid set forth in claim 11 further comprising a section of water-pervious material covering said means of water-absorbent construction and joined to said body side portions to retain said means within said body.

* * * * *